(12) United States Patent
Hudnall

(10) Patent No.: US 7,294,351 B2
(45) Date of Patent: Nov. 13, 2007

(54) COMPOSITION CONTAINING FRACTIONATED BEE PROPOLIS

(75) Inventor: Michael Hudnall, Phoenix, AZ (US)

(73) Assignee: CC Pollen Co., Phoenix, AZ (US)

( * ) Notice: Subject to any disclaimer, the term of this patent is extended or adjusted under 35 U.S.C. 154(b) by 0 days.

(21) Appl. No.: 11/287,279

(22) Filed: Nov. 28, 2005

(65) Prior Publication Data

US 2007/0122426 A1  May 31, 2007

(51) Int. Cl.
*A61K 35/64* (2006.01)

(52) U.S. Cl. .................. 424/539; 424/400; 424/405; 424/537

(58) Field of Classification Search ............... 424/400, 424/405, 539, 537
See application file for complete search history.

(56) References Cited

U.S. PATENT DOCUMENTS

| | | | |
|---|---|---|---|
| 4,382,886 A | 5/1983 | Sosnowski | |
| 5,529,779 A | 6/1996 | Hamada et al. | |
| 5,561,116 A * | 10/1996 | Nakamura et al. | 514/23 |
| 5,922,324 A | 7/1999 | Aga et al. | |
| 6,153,227 A | 11/2000 | Shibuya et al. | |
| 6,153,228 A * | 11/2000 | Shibuya et al. | 424/539 |
| 6,190,703 B1 | 2/2001 | Hamanaka | |

OTHER PUBLICATIONS

Usia et al., "Constituents of Chinese Porpolis and Their Antiproliferative Activities", J. Natural Products, 2002 65:673-676.*

Elmberger, P.G., et al.; "Conditions for Quantitation of Dolichyl Phosphate, Dolichol, Ubiquinone and Cholesterol by HPLC;" *Biomedical Chromatgraphy*;vol. 3, No. 1, pp. 20-28. (1989) (Discussed in the Specification).

Huang, D., et al.; "High-Throughput Assay of Oxygen Radical Absorbance Capacity (ORAC) Using a Multichannel Liquid Handling System Coupled with a Microplate Fluorescence Reader in 96-Well Format;"*Journal of Agricultural and Food Chemistry*; vol. 50, No. 16, pp. 4437-4444. (2002) (Discussed in the Specification).

Woisky R. G., et al.; "Analysis of propolis: some parameters and procedures for chemical quality control;" *Journal of Apicultural Research*; vol. 37, No. 2, pp. 99-105. (1998).

Greenaway, W., et al.; "The Composition and Plant Origins of Propolis: A Report of Work at Oxford;" *Article*; pp. 107-118, (1990).

Bonvehi, J. S., et al.; "The Composition, Active Components and Bacteriostatic Activity of Propolis in Dietetics;" JAOCS, vol. 71, No. 5, pp. 529-532. (1994).

Jiménez, J. J., et al.; "Quality assurance of commercial beeswax Part I. Gas chromatography—electron impact ionization mass spectrometry of hydrocarbons and monoesters;" *Journal of Chromatography A*; vol. 1024, pp. 147-154. (2004).

Aichholz, R. et al.; "Investigation of combwax of honeybees with high-temperature gas chromatography and high-temperature gas chromatography—chemical ionization mass spectrometry II: High-temperature gas chromatography—chemical ionization mass spectrometry;" *Journal of Chromatography A*; vol. 883, pp. 75-88. (2000).

Aichholz, R. et al.; "Investigation of combwax of honeybees with high-temperature gas chromatography and high-temperature gas chromatography—chemical ionization mass spectrometry I: High-temperature gas chromatography;" *Journal of Chromatography A*; vol. 855, pp. 601-615. (1999).

* cited by examiner

*Primary Examiner*—Ruth A Davis
(74) *Attorney, Agent, or Firm*—Edwards Angell Palmer & Dodge LLP (57) ABSTRACT

A composition containing fractioned propolis wax isolated without the use of solvents. The composition contains about 24-50 mg/g of total polyphenols, about 11-18% resins, about 77-87% wax, about 2.4-5.0% polyphenols and about 0-5% other materials.

6 Claims, 4 Drawing Sheets

FIG. 2: Effectiveness of Fractionated Propolis Wax and Regular Beeswax vs Pseudomonas aeruginosa FIG. 3: Effectiveness of Fractionated Propolis Wax and Regular Beeswax vs Staphylococcus aureus FIG. 4: Effectiveness of Fractionated Propolis Wax and Regular Beeswax vs Streptococcus mutans

COMPOSITION CONTAINING FRACTIONATED BEE PROPOLIS

CROSS REFERENCE

This application is cross referenced with an application entitled "Dental Floss Having a Fractionated Bee Propolis Coating" incorporated by reference herein and filed on even date herewith.

BACKGROUND OF THE INVENTION

Propolis is resinous and contains a complex mixture of substances collected by honeybees. Propolis has a color varying from greenish yellow to dark brown. Bees use propolis to seal holes in their hives, exclude draught, protect against external invaders and mummify the carcasses of predators. The amount of propolis available from a bee colony is related to the hive structure used in the honey and pollen gathering operations.

Bees collect resins from numerous different plant species, thus the chemical composition of propolis varies greatly and depends directly on the local flora and phenology of the host plants and indirectly on the locality and time of collection. It is believed that part of the substances collected undergoes chemical alteration by bee enzymes prior to incorporation in propolis, making propolis a substance considered to be of both plant and animal origin. Specifically, bees mix the plant exudates (including resins, waxes and oils collected from different parts of plants and trees including branches, flowers, pollen and buds) with beeswax (which bees secrete through glands located near the hypopharygeal region of the bees' bodies) and β-glucosidase they secrete during plant exudate collection and small amounts of sugar, which results in whole propolis. Due to differences in chemical composition, the biological activity of propolis also differs with the geographic area.

Propolis is collected and sold, but methods of preparation and the resulting product vary considerably. In most countries, tinctures of propolis are the most common form of propolis available to consumers.

While chemical composition varies, propolis is generally composed of about 45% resin, 35% wax and 20% inert material. More specifically, propolis constituents include about 10% essential oils, 5% pollen, and 15% various organic polyphenolic compounds including, flavonoids and phenolic acids. Propolis is most often purified-by extraction with solvents, particularly ethanolic extracts of propolis. The extraction process removes the wax and the inert material, and preserves the resinous phenolic fraction. A multi-step extraction with ethanol can result in dewaxed propolis extracts rich in polyphenolic components.

There is substantial evidence that propolis has antiseptic, antifungal, antibacterial, antiviral, anti-inflammatory and antioxidant properties. The polyphenolic content of propolis is considered to contribute more to the observed healing effects than other propolis constituents. Propolis has a long history of use in folk medicine.

Alcohols, aldehydes, aliphatic and aromatic acids, aliphatic and aromatic esters, chalcones, terpenoids, steroids, sugars, amino acids as well as large numbers of flavonoids have been identified in propolis. The flavonoids, aromatic acids and phenolic derivatives are believed to be the main components having therapeutic effects with flavonoids and phenolic acid esters, being known for their antibacterial and antioxidant properties.

Intact propolis, however, is not useful in food products because it generally contains large amounts of contaminants and is barely soluble in water. Currently, propolis is added in the form of extracts to food and health care products. Because the resin portion of whole propolis contains most of the polyphenolic compounds, commercially it has been desirous to obtain resin extracts from which the polyphenolic compounds are further extracted, with the less desirous wax portion becoming the waste product. Up until now, there has been no use for the wax portion of propolis and thus it remains as the waste product of refined propolis.

SUMMARY OF THE INVENTION

The fractionated propolis wax of the present invention is an integral, multi-constituent fraction of whole propolis that differs from and is more complex than regular beeswax. The fractionated propolis wax contains beeswax, plant waxes, essential oils from plants and propolis resin residue from whole propolis. It also contains bee glandular secretions that split plant resin glycosides into individual free aglycons.

The fractionated propolis wax of the present invention contains about 2.4-5% polyphenols; about 11-18% resin; about 77-87% wax. Preferably the fractionated propolis wax of the present invention contains about 3-4 % polyphenols; about 13-15% resin; and about 79-84% wax.

Several constituents of fractionated propolis wax of the present invention, specifically tree resin, plant waxes and plant oils, contribute to the total polyphenol content of the fractionated propolis wax, as the polyphenols have a plant origin. The fractionated propolis wax also exhibits antioxidant and antimicrobial activity. The fractionated propolis wax contains a range of about 24-50 mg/g of total polyphenols.

DETAILED DESCRIPTION OF THE INVENTION

The present invention relates to the wax fraction of propolis and all products containing the wax fraction of propolis. More specifically, the invention relates to the wax fraction of propolis obtained from whole propolis without any solvent or melting solution. The wax fraction of the present invention is separated based on the specific gravity difference with the resin fraction after whole propolis has been melted and mixed with mixing blades.

The following definitions are used in this application:

Whole propolis: a raw mixture of plant exudates (including resins, waxes and oils collected from different parts of plants and trees including branches, flowers, pollen and buds) with beeswax (which bees secrete through glands in their necks) and β-glucosidase, which bees secrete during plant exudate collection, small amounts of sugar, and any other impurities collected or produced by bees.

Beeswax: a wax secreted by bees through glands in their necks. The term refers to the wax found in honeycombs.

Polyphenol: any variety of phenolic compounds that may be found in propolis.

Fractionated propolis wax: a lighter wax portion that is formed based on specific gravity when whole propolis is melted and mixed.

Fractionated propolis resin: a heavier resin portion that is formed based on specific gravity when whole propolis is melted and mixed.

An exemplary method for making the composition of the present invention is as follows:

Whole propolis, in an amount of 600 to 700 kg, is first placed in a steam-jacketed double-walled heated mixing vessel. The temperature of the mixing vessel is raised to about 190-200° F., which is hot enough to melt whole propolis. The whole propolis is agitated with mixing blade paddles for 5 to 6 hours, resulting in the mixing of the melted whole propolis. The melted mixture is continuously mixed with the mixing blades throughout the process.

The melted whole propolis fractionates into two portions, a lighter wax fraction and a heavier resin fraction. The melted propolis wax portion forms a separation layer above the melted propolis resin portion in the mixing vessel due to specific gravity differences between the resin fraction and the wax fraction.

At an appropriate time, the mixing blades are stopped for about 30 minutes and then the top separation layer containing the propolis wax fraction is pumped off the mixture by an air-powered motor driven pump with an impeller. The propolis wax fraction is then sieved through a USA standard testing sieve #100 CN filter to yield fractionated propolis wax and then the fractionated propolis wax is solidified and stored.

No solvent or melting solution is used during the fractionating process. Further no resin is intentionally added to the fractionated propolis wax after it has been separated and removed from whole propolis.

Fractionated propolis wax is not merely beeswax imbued with propolis resin; it is an integral, multi-constituent fraction of whole propolis that is different and more complex than regular beeswax. Fractionated propolis wax contains beeswax, plant waxes, essential oils from plants, propolis resin residue from the starting whole propolis and polyphenols. It also contains bee glandular secretions that split plant resin glycosides into individual free aglycons.

The fractionated propolis wax of the present invention is defined generally in terms of resin, polyphenols, wax and other components. The fractionated propolis wax also has many organic compounds, some in significant quantities but many others in trace amounts.

To determine the possible range of wax in the fractionated propolis wax of the present invention, several samples of the fractionated propolis wax were tested for the total wax content in a laboratory procedure known as the Soxhlet-Fat extraction method, a method often used to determine fat content. A brief explanation of one Soxhlet-Fat extraction method will be given for fat determination, but is applicable to wax content determination as well.

The following equipment is used to perform the method: extraction thimbles, 25×80 mm, as fat can be removed from thimbles by washing with several 20 mL aliquots of ether, then dried in a 100° C. air oven; a Soxhlet extraction apparatus with extraction tubes of 30 mm internal diameter; filter paper, Whatman #541 (9 cm) or equivalent; aluminum dishes, disposable, approximately 60 mm diameter×18 mm deep; glass beads, hollow, perforated, 4 mm in diameter; and extraction flasks, 125 mL, with a flat-bottom.

In this method, petroleum ether; diethyl ether, anhydrous; and sea sand—washed and ignited are used as reagents.

The Soxhlet-Fat extraction method is as follows: First weigh 3-4 g of a sample like a liquid or semiliquid sample onto a small disposable aluminum dish. Next, add a small amount of sand into the sample using a glass rod. Spread the mixture across the bottom of the dish and wipe the rod clean with strips of filter paper and add these to the filter containing the sample and the sand. Next dry in an air oven at 125° C. for 1.5 hours and place in a thimble. Accurately weigh a dried extraction flask.

For the extraction process use petroleum ether or diethyl ether depending on the sample. Put about 75 mL of ether into each flask. Put the thimble with the sample into the soxhlet and connect the flask to the soxhlet and the soxhlet to the condenser. Adjust the water bath temperature to obtain a condensation rate of at least 5-6 drops per second and extract for 4 hours.

At the completion of the extraction, place the flask on a steam bath under a hood and evaporate the ether until no odor of it is detectable. Dry the flask and contents in an air oven for 30 minutes at 100° C., cool and weigh.

The percent of fat content or wax content is determined by formula (1):

(1):

$$\% \text{ Fat}/\text{Wax} = \frac{\text{Final flask weight} - \text{Initial flask weight}}{\text{Sample weight}} \times 100.$$

Additional references for the Soxhlet extraction method are given in AOAC 960.39, 920.39 and AOCS Ba 3-38.

In the present invention, samples were analyzed as hexane extractables. The following results were obtained and are shown in TABLE 1.

TABLE 1

| Sample | Total wax content (%) |
|--------|----------------------|
| 001    | 79.7                 |
| 002    | 81.8                 |
| 003    | 81.5                 |
| 004    | 83.9                 |
| 005    | 80.0                 |
| 006    | 81.4                 |

It was found that the general wax content in the fractionated propolis wax is about 77-87% wax. The preferred range of wax is about 79-84% with the more preferred range being from about 80-82%.

The fractionated propolis wax of the present invention contains a range of 24-50 mg/g of total polyphenols. Regular crude, yellow and refined (USP grade) beeswax has been found to contain very little, if any, polyphenols. The polyphenol content of propolis wax is one of the most accurate parameters for defining the material, as well as for delineating the differences between the material and regular beeswax. Several constituents of the fractionated propolis wax, specifically tree resin, plant waxes and plant oils, contribute to the total polyphenol content of the fractionated propolis wax.

The chemical composition of the fractionated propolis wax of the present invention can be defined generally as containing about 11-18% resin, about 2.4-5% polyphenols, about 77-87% wax and about 0-5% other constituents. Preferably the fractionated propolis wax of the present invention contains about 13-15% resin, about 3-4% polyphenols, about 79-84% wax and about 2-3% other materials.

As far as the organic compounds in the fractionated propolis wax of the present invention, one sample of the fractionated propolis wax was analyzed for organic components. In brief, the following analytical methods were used on a sample of the fractionated propolis wax: Long chain aldehyde and alcohol analysis was performed by hexane-ethyl acetate extraction followed by sequential periodate oxidation and p-bromo-phenol derivatization of resultant fatty acids. HPLC analysis using ODS2 5 μm (300×2.5 mm) and 30 minute gradient elution with 6% ACN (25 mM TBAH buffered) changing linearly to 60% ACN (25 mM TBAH buffered), with photodiode array detection and signal extraction at 280 nm. Free saturated hydrocarbons and alkyl glycerols were analyzed pre and post saponification by GC-MS performed on a 1:10 dilution/extraction in tetrachloromethane on a 10 μl injection by Gas Chromatography on a stationary phase of BPX5, 0.25 m film: column: 30 m×0.1 mm ID. Oven program: Initial Temp: 50° C., 1 minute; Rate 1: 30° C./min; Final Temp: 320° C., 2 minutes; Detector Type: MS in positive ion; Temperature: 320° C.; Carrier Gas: He, 23 psi.; Average Linear Velocity: 30 cm/sec at 50° C.; Injection Mode: Split; Split Ratio: 100:1; Injection Volume: 0.1 μL; Injection Temperature: 250° C.; Linear Type: 4 mm ID Single Taper; Identification/quantification by external standards method; standards obtained from Sigma-Aldrich. Sterol analysis performed by method of Elmberger PG, Eggens I, Dallner G "Conditions for quantification of dolichyl phosphate, dolichol, ubiquinone and cholesterol by HPLC" as published by Biomed. Chromatography, 1989, Vol. 3, No. 1, pp. 20-28. Samples were subjected to alkaline hydrolysis and clean-up on a Sep-pak C18 cartridge. Chromatography on a column (6 cm×4.6 mm) of Hypersil ODS (3 mum), with detection at 214 nm, gradient elution (2 ml min-1) was used from 0 to 70% of hexane-propan-2-ol (I)-methanol (II) (I:2:3) in I-II-$H_2O$ (8:12:1) (containing 20 mM-$H_3PO_4$ for dolichyl phosphate). Ergosterol and dolichol 23 were used as internal standards.

A sample of the fractionated propolis wax of the present invention, analyzed using the above methods, was found to contain the organic compounds shown in TABLE 2.

TABLE 2

| Analyte | Amount |
| --- | --- |
| C22-C30 aldehydes | 302.7 mg/g |
| C18-C22 aldehydes | 128.4 mg/g |
| C18-C28 alcohols | 55.94 mg/g |
| C18-C28 acids | 71.68 mg/g |
| C20-C28 saturated hydrocarbons | 31.49 mg/g |
| Acyl/alkyl glycerols | 223.4 mg/g |
| Ergosterol | 0.684 mgc/g |
| Fecosterol | 0.220 mgc/g |
| Episterol | 0.249 mgc/g |
| Lanosterol | 0.914 mgc/g |
| Carbohydrate (by AOAC 971.18) | Less than 1 mg/g |
| Sugars (by AOAC 923.09) | Less than 1 mg/g |
| Total dietary fiber (by AOAC 991.43) | Less than 1 mg/g |
| Protein (by Kjeldahl nitrogen) | Less than 1 mg/g |
| Fat - total (by hexane extraction) | 813.61 mg/g |
| Calories (by calculation) | 7.322 kcal/g |

Thus, fractionated propolis wax is different than pure beeswax that is secreted from the wax glands of bees. Fractionated propolis wax is derived from raw propolis and contains a high resin fraction, while regular beeswax is pure wax which contains no propolis resin biochemicals incorporated into it.

Other useful assays to quantify the contents or properties of fractionated propolis wax, include a total polyphenol assay, an ORAC assay of antioxidant activity and an antimicrobial assay.

Total Polyphenol Assay

Total polyphenols is a test that measures the total quantity of polyphenol biochemicals present in a substance, as polyphenols are useful marker compounds for the comparative analysis of fractionated propolis wax and regular beeswax.

Fractionated propolis wax has between 24-50 mg/g of polyphenols while regular beeswax contains very little quantities of polyphenols.

In the assay below, total polyphenol readings are the sum of the hydrophilic polyphenol assay results and the lipophilic polyphenol assay results. The following laboratory protocols were used.

The hydro phenolics were extracted as follows: First, weighed 0.5 g into 50 ml polypropylene tube. Next melted samples in a heated water bath; and extracted by adding 20 ml of Acetone: water (50:50) to each tube; shook for 1 hour, centrifuged at approximately 4000 rpm for 10 minutes at 20° C. The procedure was run on COBAS using Gallic Acid Standards.

The lipo phenolics assay protocol is listed below: first weighed 0.5 g of a sample into a 50 ml polypropylene tube. Next melted samples in a heated water bath; and extracted by adding 10 ml hexane: ethyl acetate (75:25) to each tube; shook 1 hour; centrifuged at approximately 4000 rpm for 10 minutes at 20° C. Next filtered the supernatant into clean tubes and dry down with nitrogen. Then reconstituted samples in 4 ml acetone (vortex and sonicate to ensure complete reconstitution); centrifuged then transferred 3 ml to clean tubes; and added 3 ml 7% RMCD in distilled water to each tube and vortexed. The phenolic procedure was run on COBAS using Gallic Acid Ester standards in 7% RMCD distilled water.

The following results, shown in TABLE 3, were obtained:

TABLE 3

| Sample ID | Material | Hydro Phenolics (mg/g) | Lipo Phenolics (mg/g) | Total Phenolics (mg/g) |
| --- | --- | --- | --- | --- |
| 007 | Frac. Prop. Wax | 16.84 | 9.70 | 25.54 |
| 008 | Frac. Prop. Wax | 30.22 | 18.43 | 48.65 |
| 009 | Frac. Prop. Wax | 29.89 | 15.28 | 45.17 |
| 010 | Frac. Prop. Wax | 29.57 | 16.63 | 46.20 |
| 011 | Frac. Prop. Wax | 22.66 | 13.81 | 36.47 |
| 012 | Frac. Prop. Wax | 19.57 | 9.19 | 28.76 |
| 013 | Unref beeswax | 0.46 | 0.28 | 0.74 |
| 014 | Yell Ref. BeesW | 0.37 | 0.27 | 0.64 |
| 015 | USP Grade highly refined beeswax | Not Detected | Not Detected | Not Detected |

Sample 013 was Crude (unrefined) beeswax; sample 014 was Yellow (refined) beeswax; sample 015 was USP Grade (highly refined) beeswax; and all other samples were samples of the fractionated propolis wax of the present invention.

In another trial, the percent of resin in one sample of the fractionated propolis wax was calculated based on the polyphenol content. The trial result was that there was 15.84 mg/g of polyphenols in the fractionated propolis wax. This compares with almost no polyphenols in regular pure beeswax and 135.68 mg/g of polyphenols in pure propolis resin.

By assumption, if regular pure beeswax can contains 0 mg/g of polyphenols and pure propolis resin contains 100% resin and no beeswax, its polyphenol concentration (138.68 mg/g) correlates to 100% propolis resin. By simple calculation, it is then reasonable to estimate that fractionated propolis wax contains about 11.67% propolis resin (15.84/135.68) because the polyphenols exist with the resin portion in propolis. This figure is an estimate based on polyphenol content, relative to pure wax (0% polyphenols) and pure resin (100% polyphenols).

ORAC Assay

The ORAC (Oxygen Radical Absorbance Capacity) assay is a laboratory method that accurately measures the antioxidant activity of substances. One ORAC method has been described in the article "High-Thruput Assay of Oxygen Radical Absorbance Capacity (ORAC) using a Multichannel Liquid Handling System Coupled with a Microplate Fluorescence Reader in 96-Well Format" by Huang et al. in the *Journal of Agricultural and Food Chemistry*, Vol. 50, p. 4437-4444 (2002). This method uses a multichannel liquid handling system instead of a COBAS FARA II anlyzer. In the method the phenolic compounds dissolved in an acetone-water mixture and diluted with a potassium phosphate buffer for analysis.

The ORAC measurement differs from the Total Polyphenol methodology in that is measures antioxidant activity of a substance, rather than the quantity of specific biochemicals present in a substance. The results of the comparative ORAC assays are given in TABLE 4.

TABLE 4

| Sample ID | Material | Hydro ORAC (μmole TE/g) | Lipo ORAC (μmole TE/g) | Total ORAC (μmole TE/g) |
|---|---|---|---|---|
| 016 | Frac. Prop. Wax | 377 | 551 | 928 |
| 017 | Frac. Prop. Wax | 509 | 864 | 1373 |
| 018 | Frac. Prop. Wax | 419 | 816 | 1235 |
| 019 | Frac. Prop. Wax | 523 | 950 | 1473 |
| 020 | Unref beeswax | 11 | 14 | 25 |
| 021 | Yell Ref. BeesW | 9 | 15 | 24 |
| 022 | USP Grade highly refined beeswax | 1 | 3 | 4 |

Sample 020 was Crude (unrefined) beeswax; sample 021 was Yellow (refined) beeswax; sample 022 was USP Grade (highly refined) beeswax; and all other samples were samples of the fractionated propolis wax of the present invention.

In another trial, the percent of resin in fractionated propolis wax was calculated based on the ORAC value. The trial yielded the following results shown in TABLE 5.

TABLE 5

| Substance | ORAC-Hydro (μmoleTE/g) | ORAC-Lipo (μmoleTE/g) | % of Total Hydro/Lipo | ORAC Total (μmoleTE/g) |
|---|---|---|---|---|
| Regular pure beeswax | None | 2 | — | 2 |
| Fractionated propolis wax | 309 | 868 | 26/74 | 1,177 |
| Pure propolis resin | 2,459 | 7,215 | 25/75 | 9,674 |

In the ORAC assay, regular beeswax registered no ORAC units (μmoleTE/g) in the water soluble fraction, 2 ORAC units in the lipid soluble fraction, for a Total ORAC score of 2. Fractionated propolis wax scored 309 ORAC units in the water soluble ORAC fraction, 868 ORAC units in the lipid soluble fraction, for a total of 1,177 ORAC units. In reference, pure propolis resin contains 2,459 ORAC units in the water soluble fraction, 7,215 ORAC units in the lipid soluble fraction, for a total of 9,674 ORAC units.

Fractionated propolis wax contains a combination of beeswax and resin. The results above show that pure propolis resin exhibits 9,674 total ORAC units of antioxidant activity. Since the pure propolis resin is 100% resin, this ORAC score correlates with the value of 100% propolis resin for the purpose of comparison. The results above also show that regular pure beeswax exhibits no (0%) significant antioxidant activity. So, regular pure beeswax can be assigned a baseline of (0%) value for comparative purposes. The resulting estimate shows fractionated propolis wax contains about 12.67% propolis resin (1,177/9,674), which is an estimate based on the relative ORAC value between the pure resin (100% value) and the pure beeswax (0% value).

Antimicrobial Assays

Several experiments were performed to determine the antimicrobial effects of fractionated propolis wax and regular beeswax against yeast/fungus *Candida albicans*, and three strains of pathogenic bacteria, *Pseudomonas aeruginosa*, *Staphylococcus aureus* and *Streptococcus mutans*.

In these experiments, the following materials were used: fractionated propolis wax and regular beeswax both from CC Pollen; Butterfield's buffer (BFB), Plate Count agar (PCA), and Potato Dextrose agar (PDA) all from Kalmar Laboratories; *Staphylococcus aureus* (ATCC 6538); *Candida albicans* (ATCC 10231); *Pseudomonas aeruginosa* (ATCC 9027); *Streptococcus mutans* (ATCC 25175); a sterilized cheese grater; an incubator, 35° C. aerobic; and an incubator, 25° C. aerobic.

The following procedures were performed in a Biosafety level II hood, using proper aseptic techniques. Fractionated propolis wax was maintained at 4° C. to facilitate grating. The fractionated propolis wax was grated using a flame sterilized cheese grater. Ten aliquots of grated fractionated propolis wax and regular beeswax were weighted and suspended in 19 ml of sterile BFB. The fractionated propolis wax and regular beeswax are represented in FIGS. 1-4.

Cultures of *Staphylococcus aureus, Candida albicans, Pseudomonas aeruginosa,* and *Streptococcus mutans* were used to make stock suspensions and diluted in sterile BFB to provide a final concentration of $1 \times 10^5$ to $5 \times 10^5$. The fractionated propolis wax and regular beeswax solutions were inoculated with 100 μl of the diluted stock suspensions.

Positive controls were prepared in triplicate by inoculating sterile BFB with the diluted stock suspensions. The average concentrations of the positive controls are represented in FIGS. 1-4 as "Positive Control." Negative controls were prepared in triplicate by adding 100 mg of fractionated propolis wax and regular beeswax to separate tubes without the addition of any microorganisms.

Samples for initial bacterial concentrations were plated on PCA and incubated at 35° C. Samples for the initial yeast concentrations were planted on PDA and incubated at 25° C. Once the challenge organisms were added to the fractionated propolis wax and regular beeswax solutions and the initial concentrations were verified; the inoculated samples were maintained at room temperature under standard fluorescent lighting for 24 hours.

Post test samples were collected and tested the same as the samples for initial bacterial concentrations and initial yeast concentrations.

TABLES 6-13 show the data collected for each challenge organism and the antimicrobial effectiveness of fractionated propolis wax and regular beeswax respectively. The results are that the fractionated propolis wax exhibited significant antimicrobial properties against all challenge organisms. In contrast, the regular beeswax did not exhibit antimicrobial properties against the challenge organisms.

TABLE 6

Fractionated propolis wax v. *Candida albicans*

| Sample Number | Conc. Of Frac. Prop. Wax (mg/ml) | Initial Candida albicans conc. (CFU/ml) | Post Candida albicans conc. (CFU/ml) | % Kill |
|---|---|---|---|---|
| Pos. Control | 0 | 34,500 | 30,200 | 12.5 |
| 1 | 1.48 | 37,000 | 38,300 | 0.0 |
| 2 | 2.91 | 33,000 | 35,000 | 0.0 |
| 3 | 5.34 | 33,500 | 11,100 | 66.9 |
| 4 | 10.69 | 34,300 | 11,300 | 67.1 |
| 5 | 18.03 | 33,800 | 10,800 | 68.0 |
| 6 | 21.74 | 36,500 | 11,000 | 69.9 |
| 7 | 33.45 | 35,500 | 10,200 | 71.3 |
| 8 | 43.48 | 33,800 | 8,100 | 76.0 |
| 9 | 52.95 | 33,400 | 8,100 | 75.7 |
| 10 | 79.43 | 33,200 | 7,800 | 76.5 |

TABLE 7

Regular Beeswax v. *Candida albicans*

| Sample Number | Conc. Of Frac. Prop. Wax (mg/ml) | Initial Candida albicans conc. (CFU/ml) | Post Candida albicans conc. (CFU/ml) | % Kill |
|---|---|---|---|---|
| Pos. Control | 0 | 35,100 | 35,100 | 0.0 |
| 1 | 1.32 | 34,000 | 31,900 | 6.2 |
| 2 | 2.93 | 31,800 | 33,300 | 0.0 |
| 3 | 5.56 | 32,400 | 32,000 | 1.2 |
| 4 | 11.25 | 32,500 | 31,000 | 4.6 |
| 5 | 17.27 | 33,000 | 33,400 | 0.0 |
| 6 | 21.83 | 33,300 | 33,000 | 0.9 |
| 7 | 33.8 | 34,300 | 32,900 | 4.1 |
| 8 | 44.14 | 32,300 | 31,800 | 1.5 |
| 9 | 52.93 | 35,800 | 33,600 | 6.1 |
| 10 | 80 | 32,800 | 32,900 | 0.0 |

TABLE 8

Fractionated propolis wax v. *Pseudomonas aeruginosa*

| Sample Number | Conc. Of Frac. Prop. Wax (mg/ml) | Initial Candida albicans conc. (CFU/ml) | Post Candida albicans conc. (CFU/ml) | % Kill |
|---|---|---|---|---|
| Pos. Control | 0 | 29,500 | 31,500 | 0 |
| 1 | 1.41 | 28,100 | 4,500 | 84.0 |
| 2 | 2.78 | 31,100 | 600 | 98.1 |
| 3 | 5.66 | 30,200 | 500 | 98.3 |
| 4 | 10.06 | 29,200 | 600 | 97.9 |
| 5 | 21.04 | 30,500 | 200 | 99.3 |
| 6 | 21.78 | 28,500 | 300 | 98.9 |
| 7 | 33.26 | 29,100 | 100 | 99.7 |
| 8 | 33.47 | 28,500 | 0 | 100.0 |
| 9 | 53.04 | 30,000 | 0 | 100.0 |
| 10 | 79.45 | 31,800 | 0 | 100.0 |

TABLE 9

Regular Beeswax v. *Pseudomonas aeruginosa*

| Sample Number | Conc. Of Frac. Prop. Wax (mg/ml) | Initial Candida albicans conc. (CFU/ml) | Post Candida albicans conc. (CFU/ml) | % Kill |
|---|---|---|---|---|
| Pos. Control | 0 | 30,400 | 35,133 | 0 |
| 1 | 1.34 | 29,100 | 34,000 | 0 |
| 2 | 2.86 | 28,700 | 34,100 | 0 |
| 3 | 5.27 | 31,000 | 34,300 | 0 |
| 4 | 11.39 | 30,500 | 32,300 | 0 |
| 5 | 17.52 | 28,500 | 35,100 | 0 |
| 6 | 23.18 | 29,500 | 33,300 | 0 |
| 7 | 34.05 | 29,800 | 34,600 | 0 |
| 8 | 43.18 | 30,100 | 32,900 | 0 |
| 9 | 52.89 | 29,700 | 34,300 | 0 |
| 10 | 78.96 | 30,200 | 34,100 | 0 |

TABLE 10

Fractionated propolis wax v. *Staphylococcus aureus*

| Sample Number | Conc. Of Frac. Prop. Wax (mg/ml) | Initial Candida albicans conc. (CFU/ml) | Post Candida albicans conc. (CFU/ml) | % Kill |
|---|---|---|---|---|
| Pos. Control | 0 | 29,900 | 39,700 | 0 |
| 1 | 1.45 | 32,500 | 32,700 | 0.0 |
| 2 | 2.92 | 33,100 | 9,300 | 71.9 |
| 3 | 5.62 | 33,500 | 3,300 | 90.1 |
| 4 | 10.61 | 34,300 | 0 | 100.0 |
| 5 | 17.56 | 33,000 | 0 | 100.0 |
| 6 | 36.41 | 34,100 | 0 | 100.0 |
| 7 | 44.2 | 33,800 | 0 | 100.0 |
| 8 | 47.83 | 33,500 | 0 | 100.0 |
| 9 | 52.97 | 32,100 | 0 | 100.0 |
| 10 | 105.23 | 33,200 | 0 | 100.0 |

TABLE 11

Regular beeswax v. *Staphylococcus aureus*

| Sample Number | Conc. Of Frac. Prop. Wax (mg/ml) | Initial Candida albicans conc. (CFU/ml) | Post Candida albicans conc. (CFU/ml) | % Kill |
|---|---|---|---|---|
| Pos. Control | 0 | 32,100 | 38,500 | 0 |
| 1 | 1.44 | 31,100 | 34,600 | 0 |
| 2 | 2.84 | 34,300 | 35,600 | 0 |
| 3 | 5.44 | 33,000 | 35,300 | 0 |
| 4 | 11.35 | 32,800 | 34,100 | 0 |
| 5 | 17.08 | 32,500 | 33,800 | 0 |
| 6 | 23.72 | 33,100 | 34,900 | 0 |
| 7 | 34.48 | 31,800 | 35,100 | 0 |
| 8 | 43.59 | 32,100 | 35,800 | 0 |
| 9 | 55.83 | 31,800 | 34,900 | 0 |
| 10 | 79.93 | 31,500 | 33,900 | 0 |

TABLE 12

Fractionated propolis wax v. *Staphylococcus mutans*

| Sample Number | Conc. Of Frac. Prop. Wax (mg/ml) | Initial Candida albicans conc. (CFU/ml) | Post Candida albicans conc. (CFU/ml) | % Kill |
|---|---|---|---|---|
| Pos. Control | 0 | 42,100 | 48,200 | 0 |
| 1 | 1.23 | 40,800 | 35,200 | 13.7 |
| 2 | 2.64 | 41,200 | 34,500 | 16.3 |
| 3 | 4.9 | 44,000 | 30,200 | 31.4 |
| 4 | 10.58 | 40,300 | 28,200 | 30.0 |
| 5 | 17.57 | 43,200 | 19,600 | 54.6 |
| 6 | 22.94 | 42,100 | 500 | 98.8 |
| 7 | 33.24 | 42,000 | 400 | 99.0 |
| 8 | 43.94 | 41,500 | 0 | 100.0 |
| 9 | 52.25 | 42,800 | 0 | 100.0 |
| 10 | 78.48 | 40,500 | 0 | 100.0 |

TABLE 13

Regular beeswax v. *Staphylococcus aureus*

| Sample Number | Conc. Of Frac. Prop. Wax (mg/ml) | Initial Candida albicans conc. (CFU/ml) | Post Candida albicans conc. (CFU/ml) | % Kill |
|---|---|---|---|---|
| Pos. Control | 0 | 44,500 | 44,200 | 0 |
| 1 | 1.17 | 42,100 | 45,100 | 0 |
| 2 | 2.67 | 40,100 | 42,900 | 0 |
| 3 | 5.46 | 43,200 | 43,800 | 0 |
| 4 | 10.95 | 40,500 | 43,900 | 0 |
| 5 | 17.41 | 42,100 | 44,500 | 0 |
| 6 | 22.29 | 41,800 | 44,600 | 0 |
| 7 | 33.87 | 41,500 | 44,900 | 0 |
| 8 | 42.13 | 43,000 | 45,000 | 0 |
| 9 | 52.91 | 41,000 | 45,100 | 0 |
| 10 | 81.06 | 40,900 | 45,900 | 0 |

FIGS. 1-4 graphically show the effect of the data in TABLES 6-13. For example, in FIG. 1, at a concentration of 5.34 mg/ml, fractionated propolis wax achieved about a 68% effectiveness (68% of the yeast/fungus was killed). This contrasts with regular beeswax shown at concentration of 80 mg/ml there was no measurable amount of effectiveness against the yeast.

Figure 1:
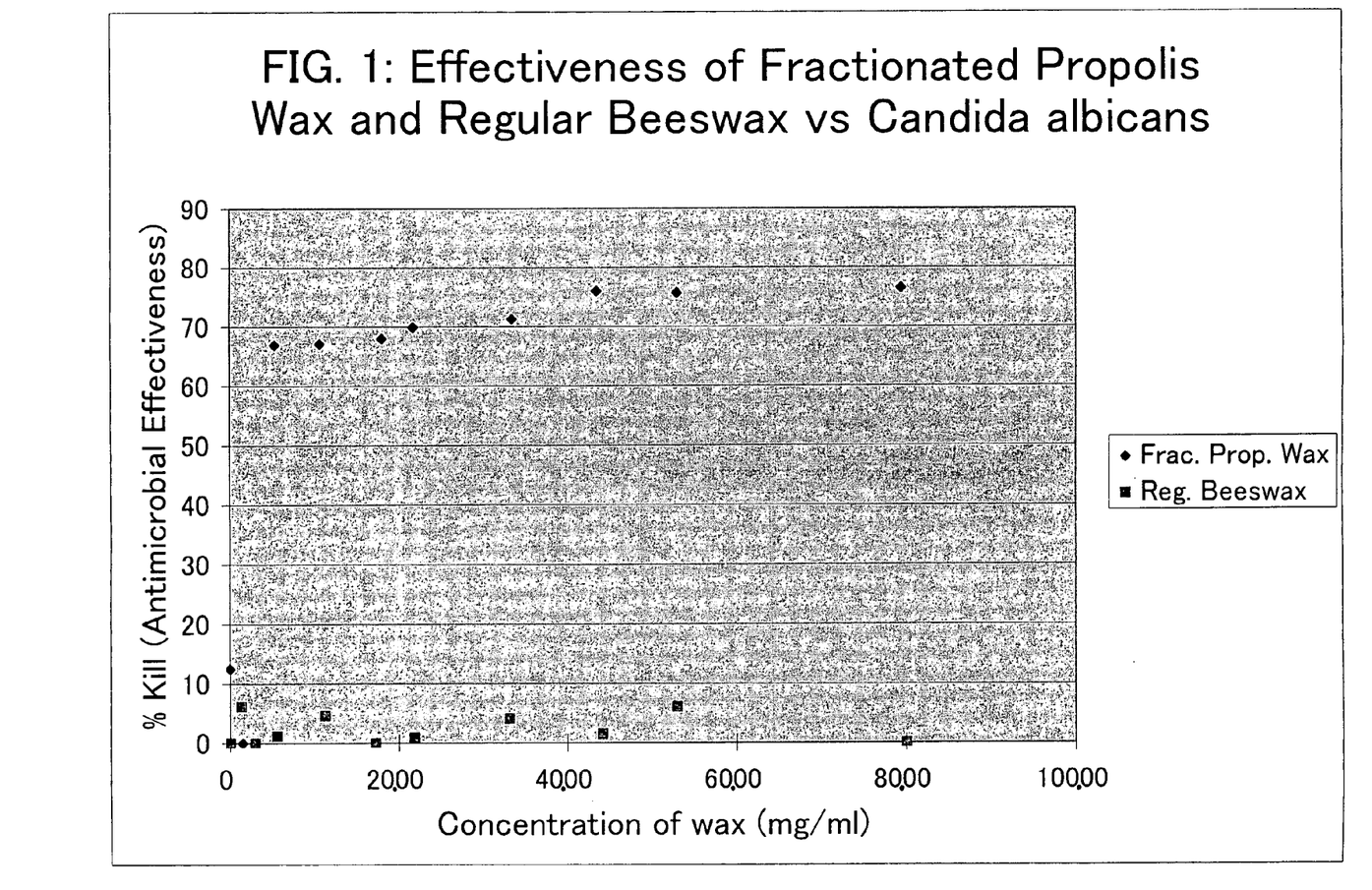
FIG. 1 shows the antimicrobial effect of the fractionated propolis wax versus regular beeswax on *Candida albicans;*
Figure 2:
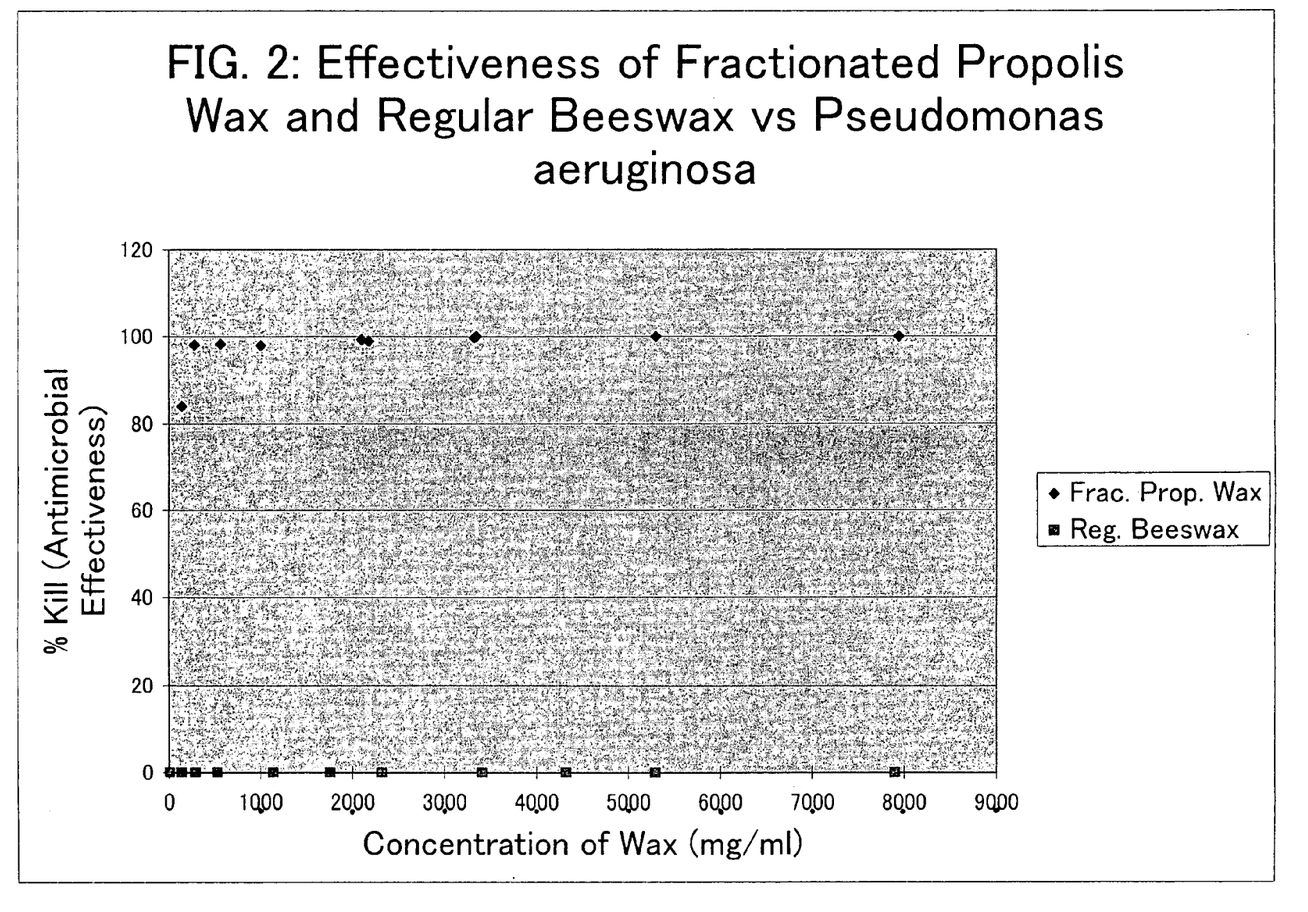
FIG. 2 shows the antimicrobial effect of the fractionated propolis wax versus regular beeswax on *Pseudomonas aeruginosa;*
Figure 3:
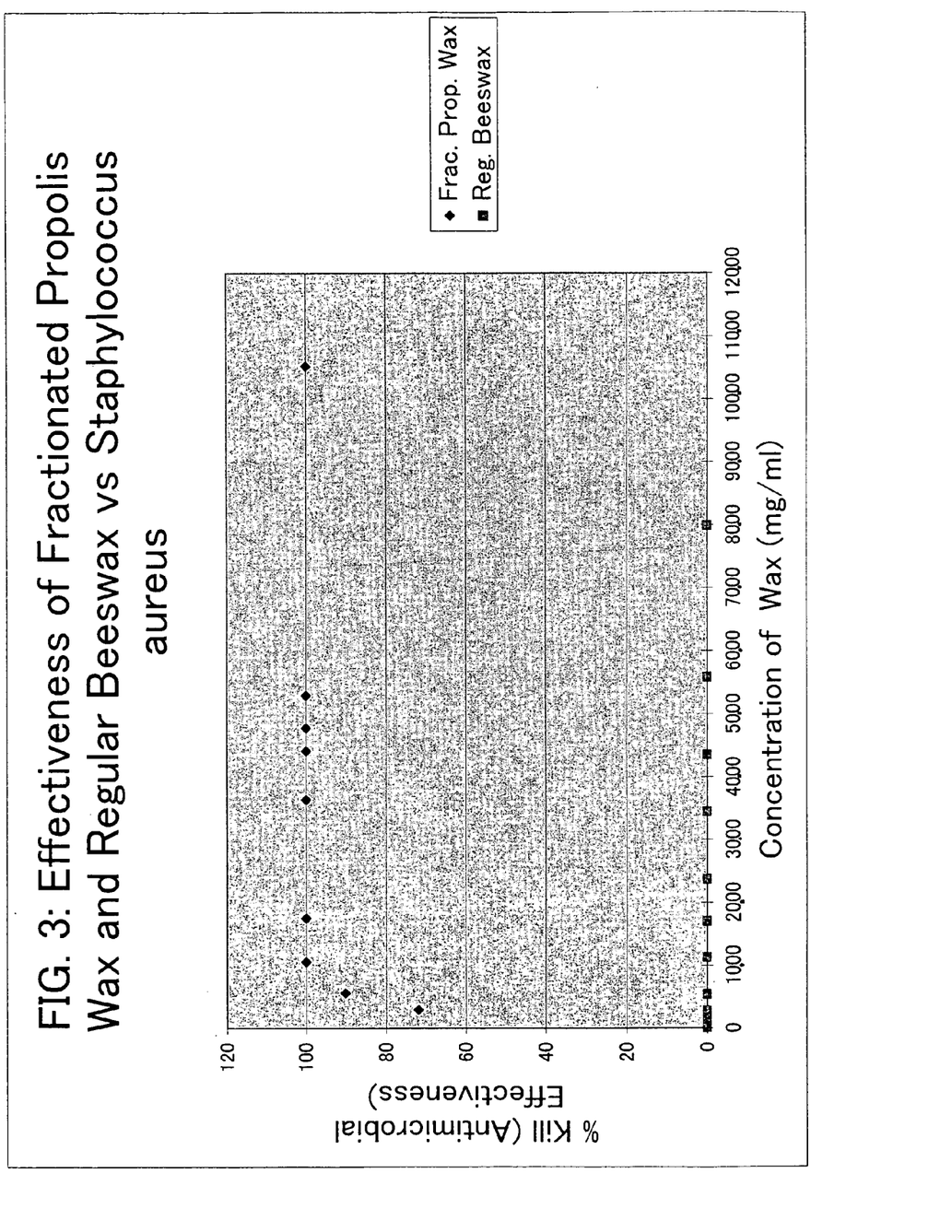
FIG. 3 shows the antimicrobial effect of the fractionated propolis wax versus regular beeswax on *Staphylococcus aureus.
Figure 4:
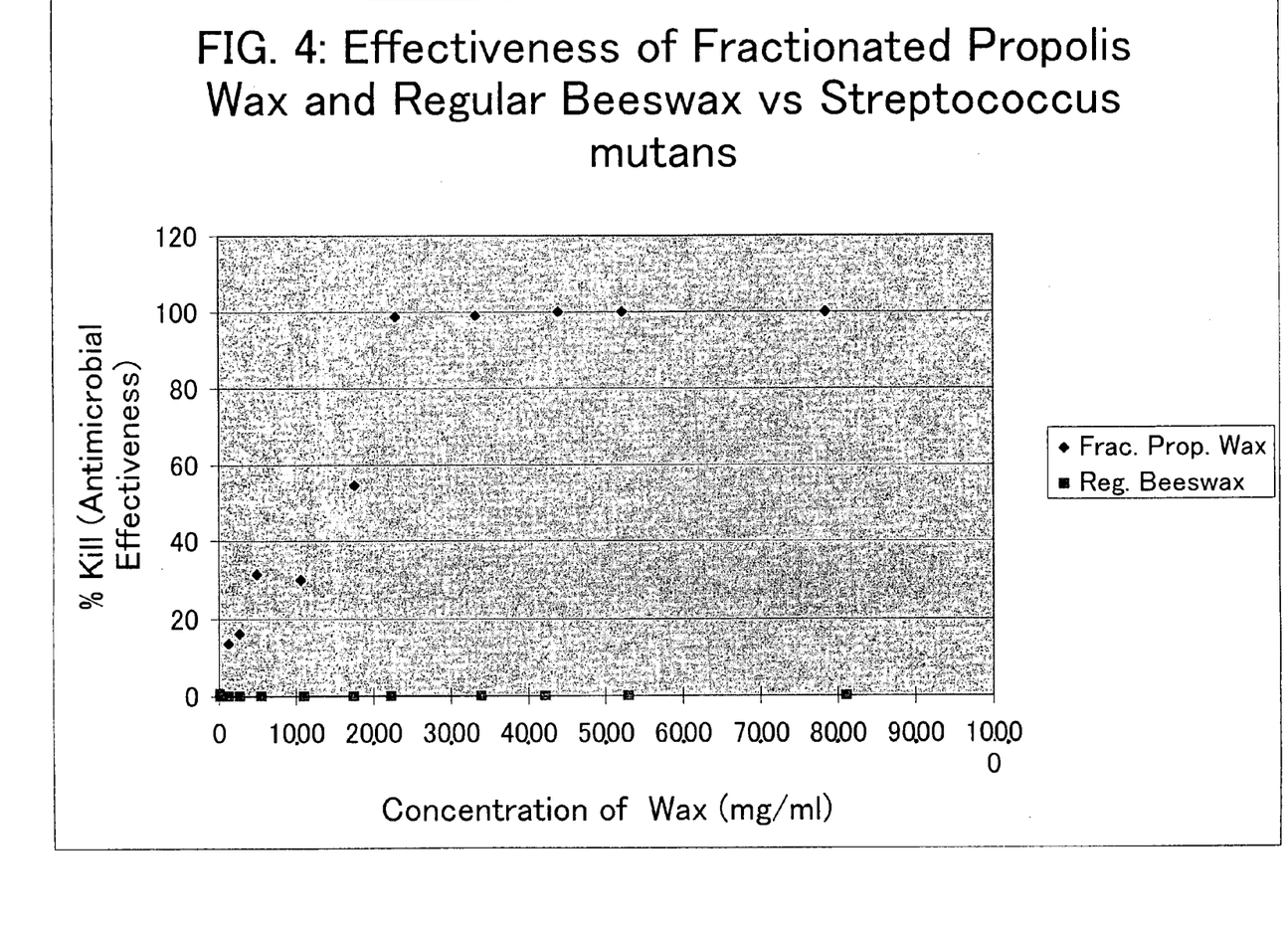
* and FIG. 4 shows the antimicrobial effect of the fractionated propolis wax versus regular beeswax on *Streptococcus mutans.*

As for FIGS. 2, 3 and 4 increased concentrations of fractionated propolis wax achieved 100% effectiveness against the three strains of pathogenic bacteria. In contrast, at nearly the same respective concentrations, regular beeswax did not achieve any measurable effectiveness.

It can be seen from these assays against a challenge organism, that fractionated propolis wax exhibits antimicrobial activity while regular beeswax does not.

While there have been illustrated and described several embodiments of the present invention, it will be apparent that various changes and modifications thereof will occur to those skilled in the art. It is intended in the appended claims to cover all such changes and modifications that fall within the true spirit and scope of the present invention.

I claim:

1. A composition of polyphenols, resin and wax made by the process comprising the steps of:
   heating whole propolis to about 190-200° F.;
   agitating the heated whole propolis until separation of whole propolis into a lighter wax layer and a heavier resin layer;
   stopping the agitating;
   removing the propolis wax fraction; and
   running the removed propolis wax fraction through a sieve.

2. The composition of claim 1, wherein the whole propolis is agitated in a steam-jacketed heating vessel.

3. The composition of claim 1, wherein the whole propolis is agitated continuously with mixing paddle blades for about 5-6 hours.

4. The composition of claim 1, wherein at the appropriate time the agitating is stopped.

5. The composition of claim 1, wherein the propolis wax fraction is sieved through a USA standard testing sieve #100 CN filter to yield fractionated propolis wax.

6. The composition of claim 1, wherein after sieving, the fractionated propolis wax is solidified.

* * * * *